United States Patent [19]

Yamabe et al.

[11] 4,275,226
[45] Jun. 23, 1981

[54] PROCESS FOR PRODUCING FLUOROVINYL ETHER

[75] Inventors: Masaaki Yamabe, Machida; Seisaku Kumai, Yokohama; Seiji Munekata, Tokyo, all of Japan

[73] Assignee: Asahi Glass Company, Ltd., Tokyo, Japan

[21] Appl. No.: 65,347

[22] Filed: Aug. 9, 1979

[30] Foreign Application Priority Data

Aug. 25, 1978 [JP] Japan ................................. 53/102686
Aug. 25, 1978 [JP] Japan ................................. 53/102687

[51] Int. Cl.³ ................. C07C 69/734; C07C 143/00; C07C 57/065; C07C 41/24
[52] U.S. Cl. ............................. 560/183; 260/543 F; 260/544 F; 260/986; 564/201; 568/674; 568/684; 568/685
[58] Field of Search ............................. 560/183, 184; 260/544 F, 5.61 N, 986, 543 F; 568/674, 681, 684, 685; 564/201

[56] References Cited

U.S. PATENT DOCUMENTS

| | | | |
|---|---|---|---|
| 3,114,778 | 12/1963 | Fritz et al. | 260/544 F |
| 3,636,172 | 1/1972 | Gardner | 252/447 |
| 4,032,566 | 6/1977 | Psarras et al. | 260/544 F |

OTHER PUBLICATIONS

Evans, F. W. et al. *J. of Organic Chemistry*, vol. 88, pp. 1939–1944 (1968).
Lo, Elizabeth S. *J. of Organic Chemistry*, vol. 36, pp. 364–366 (1971).
Blancou, H. et al. *Tetrahedron*, vol. 33, pp. 2061–2067 (1977) (See Chemical Abstracts vol. 88, #50,206j) (1978).
Kirk-Othmer "Encyclopedia of Chemical Technology" 2nd Ed. (1963) vol. 12, pp. 678–680.

*Primary Examiner*—Natalie Trousof
*Assistant Examiner*—L. Hendriksen
*Attorney, Agent, or Firm*—Oblon, Fisher, Spivak, McClelland & Maier

[57] ABSTRACT

A fluorovinyl ether having the formula $$XRfCF_2OCF=CF_2 \qquad (I)$$

wherein X represents —H, —Cl, —Br, —F, —CO$_2$R, —CONRR', —SO$_2$F,

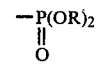

or —COF and R represents a C$_1$–C$_{10}$ alkyl group; R' represents —H or a C$_1$–C$_{10}$ alkyl group; Rf represents a C$_1$–C$_{20}$ bifunctional perfluoro-containing group is produced by reacting an iodine-containing ether having the formula $$XRfCF_2OCF_2CF_2I \qquad (II)$$

in the presence of a catalytic component selected from the group consisting of Mg, Cu, Zn, Zn-Cu, Zn-Cd, Zn-Pd, Zn-Hg, Sn, Sb, organomagnesium compounds and organolithium compounds.

15 Claims, No Drawings

PROCESS FOR PRODUCING FLUOROVINYL ETHER

BACKGROUND OF THE INVENTION

1. Field of the Invention

The present invention relates to a process for producing a fluorovinyl ether. More particularly, it relates to a novel process for producing a fluorovinyl ether by a deiodofluorination of a specific iodine-containing ether with a metal component.

2. Description of Prior Arts

It has been known that fluorovinyl ethers have been produced by a reaction of a fluoroolefin with an alkali metal alkoxide as the production of methoxytrifluoroethylene. However, such process is not suitable for the production of perfluorovinyl ethers because of low yield and difficult industrial operation.

It has been known that perfluorovinyl ethers can be produced by reacting a fluorinated acid fluoride with hexafluoropropylene epoxide and converting the product by a thermal reaction as disclosed in Japanese Patent Publication No. 1617/1963 and U.S. Pat. No. 3,114,778.

The process for using hexafluoropropylene epoxide as the starting material is remarkably effective as the process for producing fluorovinyl ethers. However, it is seriously disadvantageous because of expensive process in view of the commercial availability and the yield.

The inventors have studied to provide a process for producing fluorovinyl ehters without using hexafluoropropylene epoxide. As a result, the following facts have been found.

An iodine-containing fluoroether can be produced at high yield by reacting an acid fluoride with tetrafluoroethylene, $I_2$ and KF. The iodine-containing ether can be easily reacted with a metal such as zinc in an organic solvent and the reaction product is easily converted by heating into the corresponding fluorovinyl ether at high yield.

It has been well-known that RfI (Rf represents a perfluoroalkyl group) into R″f—CF=CF$_2$ (R″f represents a perfluoroalkyl group) with an organomagnesium compound or Zn-Cu as disclosed in J.O.C. 36 364. (1971) and Tetrahedron 33, 2061, (1977). However, the isomerization of the product is carried out to decrease the yield of the object compound and the separation and the isolation are not easy.

The isomerization of the fluorovinyl ethers having the formula XRfCF$_2$OCF=CF$_2$ is not resulted to give high selectivity in the production and the separation and the isolation of the product are remarkably easy.

The vinyl etherification by the deiodofluorination is suitable for the production of the perfluorovinyl ether.

SUMMARY OF THE INVENTION

It is an object of the present invention is to provide a process for producing a fluorovinyl ether having the formula $$XRfCF_2OCF=CF_2 \qquad (I)$$

wherein X represents —H, —Cl, —Br, —F, —CO$_2$R, —CONRR', —SO$_2$F,

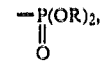

or —COF and R represents a $C_1$-$C_{10}$ alkyl group; R' represents —H or a $C_1$-$C_{10}$ alkyl group; Rf represents a $C_1$-$C_{20}$ bifunctional perfluoro-containing group which can has one or more ether bond.

Another object of the present invention is to provide a process for producing a fluorovinyl ether (I) which can be easily separated.

The foregoing and other objects of the present invention have been attained by reacting an iodine-containing ether having the formula $$XRfCF_2OCF_2CF_2I \qquad (II)$$

wherein X and Rf are defined above, with a catalytic component selected from the group consisting of Mg, Cu, Zn, Zn-Cu, Zn-Cd, Zn-Pb, Zn-Hg, Sn, Sb, organomagnesium compounds and organolithium compound in an organic solvent and then thermally reacting the resulting fluoro-organometallic compound; or reacting an iodine-containing ether (II) by a vapor phase catalytic reaction in the presence of a catalytic component selected from the group consisting of Mg, Cu, Zn, Zn-Cu, Zn-Cd, Zn-Pb, Zn-Hg, Sn and Sb.

DETAILED DESCRIPTION OF THE PREFERRED EMBODIMENTS

Suitable catalytic components used in the organic solvent include metals of Mg, Cu, Zn, Zn-Cu, Zn-Cd, Zn-Pb, Zn-Hg, Sn and Sb and organomagnesium compounds and organolithium compounds.

The metals of Zn-M (M is Cu, Cd, Pb or Hg) can be easily obtained by reacting Zn with a M metal salt such as sulfate and acetate.

When the organic solvent is used, the iodine-containing ether (II) is firstly reacted with the catalytic component to form the fluoro-organometallic compound and the resulting compound is thermally reacted into the product (I) by heating it, if necessary, after separating the organic solvent. The process for using the organic solvent is preferable to decrease a side reaction.

The iodine-containing ethers having the formula $$XRfCF_2OCF_2CF_2I \qquad (II)$$

as the starting material in the process of the present invention can be easily obtained by reacting an acid fluoride having the formula $$XRfCOF$$

with $C_2F_4$, $I_2$ and MF (M is K, Rb, and Cs) as disclosed in Japanese Patent Publication No. 13011/1972 and J. Org. Chem. 33 1839 (1968) and U.S. Pat. No. 4,032,566.

The typical reaction is as follows.

$$ROOCCF_2CF_2COF + CF_2=CF_2 \xrightarrow[KF/I_2]{medium}$$

$$ROOCCF_2CF_2OCF_2CF_2I$$

In the process of the present invention, the specific iodine-containing ether reacts with the specific metal or the specific organometallic compound in the organic solvent and the resulting fluoro-organometallic compound is thermally reacted to obtain the fluorovinyl ether. The formation and the conversion of the fluoro-organometallic compound can be simultaneously carried out if desired, to result the deiodofluorination in one step.

The fluorovinyl ether (I) can be also produced by forming the fluoro-organometallic compound in an organic medium; separating the organic medium; and then thermally reacting it to obtain the product.

The reactions can be as follows.

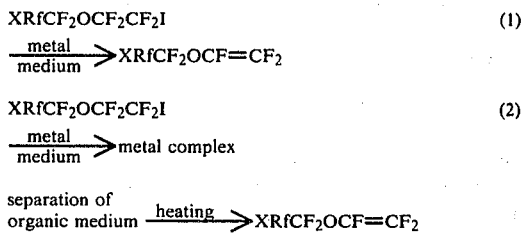

The organic medium used in the process of the present invention is preferably an inert solvent especially a polar aprotic solvent.

Suitable organic solvents include ethers such as dioxane, diphenyl ether, diethyl ether; glymes such as diglyme and tetraglyme; nitriles such as acetonitrile, benzonitrile, α-naphthonitrile, and β-naphthonitrile; and sulfolanes.

The reaction temperature is selected depending upon the kinds of iodine-containing ether, the organic solvent and the metal, and usually from about −20° C. to +250° C. The temperature for the production of the fluoro-organometallic compound is usually from about −50° C. to +200° C. preferably from about 20° C. to +130° C. The temperature for the thermal reaction of the fluoro-organometallic compound is from about +100° C. to +300° C. preferably about +150° C. to 250° C.

The molar ratio of the metal (or organometallic compound) iodine-containing ether is usually from 1:1 to 5:1 preferably from 2:1 to 3:1. It is preferable to use excess of the metal component to the iodine-containing ether. The concentration of the iodine-containing ether in the organic solvent is not critical and usually from about 2 to 50 vol.%.

The reaction is smoothly performed in said condition. The reaction time is usually from about 0.5 to 10 hours.

In the reaction, it is important to control a water content. When water is present, water reacts with the resulting organometallic compound to produce a by-product having the formula XRfCF₂OCF₂CF₂H When water is included in the organic solvent or the metal component, adverse affects such as the decrease of the reaction velocity are caused in the reaction of the iodine-containing ether with the metal component. Accordingly, water should be removed from the organic solvent and the metal component.

The thermal reaction of the fluoro-organometallic compound is preferably carried out after separating the organic solvent though it can be carried out in an organic solvent. In order to separate the resulting fluorovinyl ether from the reaction system, it is preferable to perform the thermal reaction in vacuum or in a flow of an inert gas.

The iodine-containing ethers as the starting materials are compounds having the formula XRfCF₂OCF₂CF₂I wherein X represents —H, —Cl, —Br, —F, —CO₂R, —CONRR', —SO₂F, $$-\underset{\underset{O}{\|}}{P}(OR)_2$$

or —COF and they can be selected. It is preferable to be —F, —CO₂R or —COF in view of the easy commercial availability and the utility of the object fluorovinyl ether.

In the formula, R is a C₁-C₁₀ alkyl group preferably a C₁-C₅ alkyl group; and R' is —H or R; Rf is a C₁-C₂₀ especially a C₁-C₁₀ bifunctional perfluoro-containing group which can be straight or branched and can has one or more ether bond.

The specific metal can be at least one of metals selected from the group consisting of Mg, Cu, Zn, Zn-Cu, Zn-Cd, Zn-Pb, Zn-Hg, Sn and Sb.

The specific organometallic compound is at least one of the organomagnesium compounds such as RMgBr and RMgCl; and organolithium compounds such as butyllithium and phenyllithium.

The organomagnesium compound and the organolithium compound may not be used depending upon the kind of X in the iodine-containing ether (II). For example, when X is —COOR or —CONRR', the organomagnesium compound or the organolithium compound reacts with X and accordingly, these organometallic compounds are not used.

In the normal operation, the metal and the organic solvent are charged into a reactor and a solution of the iodine-containing ether in the organic solvent is added dropwise through a dropping funnel with stirring the mixture at a desired temperature. After the addition, the reaction is continued for from 1 to 2 hours and the organic medium is distilled off under a reduced pressure and then the residue of the fluoro-organometallic compound is thermally reacted under a reduced pressure at from 150° C. to 250° C., and the resulting product is collected by a trap (dryice-ethanol). The collected product is distilled to obtain the object fluorovinyl ether (I).

The fluorovinyl ether (I) can be also obtained by the vapor phase catalytic reaction from the same starting material of the iodine-containing ether (II).

In the vapor phase catalytic reaction, the reaction temperature is usually from about 150° C. to 450° C. especially from about 200° C. to 380° C.

In the reaction, the iodine-containing ether (II) in a gaseous form is fed into a reaction filled with the specific metal component to contact them at said reaction temperature. The fixed bed, the transferring bed and the fluidized bed can be used as the filled layer of the metal component. The contact time can be a broad range such as 0.1 sec. to 600 sec. and it can be shorted at higher reaction temperature and it is preferably from about 1 sec. to 200 sec.

The reaction can be carried out without an inert gas. However, it is preferable to dilute the starting material with an inert gas such as nitrogen, helium and argon so as to prevent a side reaction. It is preferable to dilute the starting material at a ratio of the inert gas to the starting material of from 70:30 to 99:1 especially from 90:10 to 98:2.

In the filled layer of the metal component, it is possible to mix an adjuvant, an additive or a diluent such as alumina, silicon carbide, glass beads, NaI and KI. The iodine-containing ether (II) can be fed into the reaction zone after vaporizing it. When the iodine-containing ether (II) is a high boiling material, it can be fed into the reaction zone without vaporizing it and the reaction is carried out by vaporizing it on the metal component. The iodine-containing ether can be vaporized and mixed with an inert gas and the mixed gas can be fed into the reaction zone. The starting material and the inert gas can be separately fed into the reaction zone to react them during the dilution.

The metal component is preferably in a form of powder, sand or granule or the mixture thereof, because the metal component having a larger surface area is preferably in view of the efficiency and the reaction velocity. The particle size of the powder or sand form metal component is selected depending upon the gas flow rate, the diameter of the reaction tube and the form of the filled layer.

In the normal operation, the reactor having the filled layer of the metal component is externally heated to maintain a predetermined reaction temperature to vaporize the iodine-containing ether by a flash vaporizer and is fed with or without a dilution with an inert gas, into the reactor. The gas discharged from the reactor is cooled to collect the reaction product. The product is separated by a vacuum distillation to obtain the object fluorovinyl ether (I).

The present invention will be illustrated by certain examples and references which are provided for purposes of illustration only and are not intended to be limiting the present invention.

EXAMPLE 1

In a 200 ml. three necked flask, 9 g. (0.14 mole) of Zn and 35 ml. of anhydrous p-dioxane (treated by alumina) were charged and the mixture was heated at 60° C. with stirring. A solution of 30 g. (0.066 mole) of $ICF_2CF_2O(CF_2)_3COOCH_3$ in 30 ml. of anhydrous p-dioxane was added dropwise to it during 1.5 hours. The reaction was continued for 2 hours after the addition and p-dioxane was recovered by a distillation under a reduced pressure and the residue was thermally reacted at 180° C. to obtain 9.1 g. (yield 45%) of the object compound $CF_2=CFO(CF_2)_3COOCH_3$.

EXAMPLE 2

In a 200 ml. three necked flask, 6 g. (0.092 mole) of Zn-Cu (molar ratio Zn/Cu=97:3) and 40 ml. of anhydrous acetonitrile were charged. A solution of 31 g. (0.05 mole) of

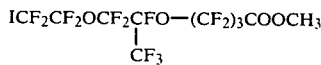

in 25 ml. of anhydrous acetonitrile was added dropwise through a dropping funnel with stirring it at room temperature. The reaction was continued for 2 hours at room temperature after the addition and acetonitrile was distilled off under a reduced pressure and the residue was thermally reacted at 150° C. to 210° C. and the product was collected by a trap cooling with dryice-ethanol to obtain 11.0 g. (yield 47%) of the object compound.

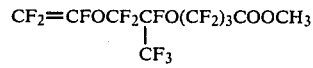

When the other metal Zn-Cd (molar ratio of Zn to Cd of 97:3); Zn-Pb (molar ratio of Zn to Pb of 97:3) or Zn-Hg (molar ratio of Zn to Hg of 93:3) was used instead of Zn-Cu the same results were attained.

EXAMPLE 3

In a 200 ml. three necked flask, 20 g. (0.047 mole) of $ICF_2CF_2OCF_2CF_2SO_2F$ and 50 ml. of anhydrous tetrahydrofuran were charged at 20° C. A solution of 0.048 mole of methylmagnesium bromide in 50 ml. of tetrahydrofuran was added dropwise through a dropping funnel during 2 hours with stirring it. The mixture was heated to 55° C. and stirred for 2 hours. The product was analyzed by a gas chromatography to find the production of 7.9 g. (yield 60%) of $CF_2=CFOCF_2CF_2SO_2F$.

EXAMPLE 4

In accordance with the process of Example 1 except using benzonitrile as the organic solvent, the process was repeated to obtain 14.7 g. (yield 73%) of the object compound $CF_2=CFO(CF_2)_3COOCH_3$.

EXAMPLE 5

In a 200 ml. three necked flask, 12 g. (0.10 mole) of Sn and 50 ml. of benzonitrile were charged and the mixture was heated at 160° C. A solution of 24.3 g. (0.044 mole) of $ICF_2CF_2O(CF_2)_5-COOCH_3$ in 30 ml. of benzonitrile was added dropwise through a dropping funnel during 1 hour with stirring. During the reaction, the distilled product was collected by a trap cooling with dryice-ethanol. After the reaction, the product dissolved in the reaction mixture was distilled out under a reduced pressure and collected by a trap cooling with dryice-ethanol. The collected product was analyzed to find the production of 9.1 g. (yield 51%) of the object compound $CF_2=CFO(CF_2)_5COOCH_3$.

EXAMPLE 6

In accordance with the process of Example 5 except using 12 g. of Sb instead of Sn, the process was repeated to obtain the object compound $CF_2=CFO(CF_2)_5COOCH_3$ (yield 43%).

EXAMPLE 7

In accordance with the process of Example 5 except using 6 g. of Cu instead of Sn, the process was repeated to obtain the object compound $CF_2=CFO(CF_2)_5COOCH_3$ (yield 37%).

EXAMPLE 8

In a 200 ml. three necked flask, 6.5 g. (0.10 mole) of Zn and 40 ml. of benzonitrile were charged and the mixture was heated to 65° C. A solution of 20 g. (0.05 mole) of $ICF_2CF_2O(CF_2)_2COOCH_3$ in 20 ml. of benzonitrile was added dropwise through a dropping funnel during 1 hour with stirring it and the mixture was further stirred at the same temperature for 2 hours and benzonitrile was distilled off and recovered under a reduced pressure. The residue was heated at 200° C. under a reduced pressure and the product was collected by a trap cooling with dryice-ethanol to obtain 9.5 g. (yield 74%) of the object compound $CF_2=CFO(CF_2)_2COOCH_3$.

EXAMPLE 9

A flash evaporator for a starting material and a gas flow control device for a diluent gas were connected to an inlet of a reactor and a trap for collecting a reaction product was connected to an outlet of the reactor of a U-shaped stainless steel pipe having an inner diameter of 8 mm and a length of 50 cm. A metal filled layer was formed for a length of about 28 cm in the U-shaped pipe and glass wool was packed at both side of the filled layer. The U-shaped pipe was immersed in a salt bath to maintain the temperature of the filled layer at a predetermined temperature.

The starting material $ICF_2CF_2O(CF_2)_3COOCH_3$ (boiling point of about 200° C./760 mm Hg) (liquid) was fed into the flash evaporator by a micropump so as to vaporize it and mixed with a diluent gas fed at a constant rate and the mixed gas was fed into the reactor through the inlet of the reactor.

The reaction temperature, and the kind of the metal were selected as shown in Table 1. The results of the reactions are shown in Table 1.

CONDITION OF REACTION diluent gas: $N_2$
concentration of starting material=

TABLE 1

| Metal | Reaction temperature (%) | Conversion (%) | Selectivity to $CF_2=CFO(CF_2)_3CO_2CH_3$ (%) |
|---|---|---|---|
| Zn | 325 | 14 | 54 |
| Zn | 350 | 53 | 48 |
| Zn | 380 | 88 | 28 |
| Zn-Cu | 300 | 13 | 47 |
| Zn-Cd | 325 | 8 | 43 |
| Zn-Pb | 325 | 15 | 42 |
| Zn-Hg | 325 | 18 | 51 |
| Sn | 220 | 8 | 72 | contact time: 8 seconds $$\frac{\text{starting material (cc)}}{\text{starting material (cc)} + N_2(cc)} \times 100 = 4\%$$

EXAMPLE 10

In accordance with the process of Example 9 using the same reactor, each reaction of $ICF_2CF_2O(CF_2)_5H$ was carried out. The results are shown in Table 2.

CONDITION OF REACTION diluent: $N_2$
concentration of starting material=4%
contact time: 8 seconds

TABLE 2

| Metal | Reaction temperature (%) | Conversion (%) | Selectivity to $CF_2=CFO(CF_2)_5H$ (%) |
|---|---|---|---|
| Zn | 350 | 51 | 73 |
| Cu | 260 | 78 | 46 |
| Fe | 350 | 33 | 62 |
| Mg | 350 | 23 | 43 |

TABLE 2-continued

| Metal | Reaction temperature (%) | Conversion (%) | Selectivity to $CF_2=CFO(CF_2)_5H$ (%) |
|---|---|---|---|
| Sb | 325 | 41 | 64 |

We claim:

1. A process for producing a fluorovinyl ether having the formula $$XR_fCF_2OCF=CF_2 \quad (I)$$

wherein X represents —H, —Cl, —Br, —F, —CO$_2$R, —CONRR', —SO$_2$F, $$-\overset{\underset{\|}{O}}{P}(OR)_2,$$

or —COF and R represents a $C_1$–$C_{10}$ alkyl group; R' represents —H or a $C_1$–$C_{10}$ alkyl group; Rf represents a $C_1$–$C_{20}$ bifunctional perfluoro-containing group which can have one or more ether bonds, which comprises reacting an iodine containing ether having the formula:

$$XR_fCF_2OCF_2CF_2I \quad (II)$$

wherein X and Rf are as defined above, in the presence of a particulate, metallic catalytic component selected from the group consisting of Mg, Cu, Zn, Sn, and Sb.

2. A process for producing a fluorovinyl ether according to claim 1 wherein the iodine-containing ether (II) is reacted with the catalytic component in an inert organic solvent and then the resulting fluoro-organometallic compound is thermally reacted to form the fluorovinyl ether (I).

3. A process for producing a fluorovinyl ether according to claim 2 wherein the thermal reaction of the resulting fluoro-organometallic compound is carried out after the removal of the organic solvent.

4. A process for producing a fluorovinyl ether according to claim 2 wherein the production of the fluoro-organometallic compound and the thermal reaction thereof are carried out by one step process.

5. A process for producing a fluorovinyl ether according to claim 2 wherein the reaction for producing the fluoro-organometallic compound is carried out at from −50° C. to +200° C.

6. A process for producing a fluorovinyl ether according to claim 2 or 3 wherein the thermal reaction of the fluoro-organometallic compound is carried out at from 100° C. to 300° C.

7. A process for producing a fluorovinyl ether according to claim 2 wherein the inert organic solvent is a polar aprotic solvent.

8. A process for producing a fluorovinyl ether according to claim 7 wherein the inert organic solvent is at least one of benzonitrile, α-naphthonitrile, β-naphthonitrile or diphenyl ether.

9. A process for producing a fluorovinyl ether according to claim 1 wherein the iodine-containing ether (II) is converted into the fluorovinyl ether (I) by a vapor phase catalytic reaction in the presence of the catalytic component.

10. A process for producing a fluorovinyl ether according to claim 9 wherein the vapor phase catalytic reaction is carried out at from 150° C. to 450° C.

11. A process for producing a fluorovinyl ether according to claim 9 wherein the reaction is carried out by diluting the iodine-containing ether (II) with an inert gas.

12. A process for producing a fluorovinyl ether according to claim 9 wherein the catalytic contact time of the iodine-containing ether (II) with the catalytic component is from 0.1 to 600 seconds.

13. A process for producing a fluorovinyl ether according to claim 9 wherein a fixed bed reactor, a transferring bed reactor or a fluidized bed reactor is used as the reactor for the vapor phase catalytic reaction.

14. A process for producing a fluorovinyl ether according to claim 11 wherein the vapor phase catalytic reaction is carried out at a ratio of inert gas to iodine-containing ether (II) of from 70:30 to 99:1.

15. A process for producing a fluorovinyl ether according to claim 1, wherein the particulate metallic component is at least one of Cu, Zn, Sn or Sb.

* * * * *